United States Patent [19]
Kuch

[11] Patent Number: 5,454,721
[45] Date of Patent: Oct. 3, 1995

[54] APPLICATION OF MULTI-MEDIA TECHNOLOGY TO NUTRITION EDUCATION AND DIET PLANNING

[76] Inventor: Nina J. Kuch, 2197 Dorset St., Shelburne, Vt. 05482

[21] Appl. No.: 176,014

[22] Filed: Dec. 30, 1993

[51] Int. Cl.$^6$ .................................................. G09B 19/00
[52] U.S. Cl. ........................ 434/127; 434/236; 434/428; 434/429
[58] Field of Search .................................... 434/127, 236, 434/238, 428–430; 364/413.13, 413.29

[56] References Cited

U.S. PATENT DOCUMENTS

| | | |
|---|---|---|
| Re. 31,200 | 4/1983 | Sukonick . |
| 4,075,769 | 2/1972 | Young . |
| 4,608,656 | 8/1986 | Tanaka et al. . |
| 4,650,218 | 3/1987 | Hawke . |
| 4,652,241 | 3/1987 | McCarty . |
| 4,828,498 | 5/1989 | Tilney . |
| 4,834,475 | 5/1989 | Robinson . |
| 4,847,604 | 7/1989 | Doyle . |
| 4,914,605 | 4/1990 | Loughmiller et al. . |
| 4,974,164 | 11/1990 | Lewis et al. . |
| 4,976,662 | 12/1990 | Clark . |
| 4,986,757 | 1/1991 | Mueller . |
| 5,044,958 | 9/1991 | Robertson et al. ................. 434/238 X |
| 5,233,520 | 8/1993 | Kretsch et al. .................... 364/413.29 |
| 5,241,671 | 8/1993 | Reed et al. . |
| 5,338,202 | 8/1994 | Saari ................................. 434/238 X |

OTHER PUBLICATIONS

Lansky D et al Am J Clin Nutr 1982; 35:727–32.
Lichtman et al N Engl J Med 1992; 327: 1893–8.
Livingstone et al BMS 1990; 300: 708–12.
Metz et al Am J Clin Natr 1991; 54:291–5.
US Pharmacopcial Convention "About Your Diabetes" 1991
Yellowlees et al BMJ 1988; 296: 1689–90.

Primary Examiner—Richard J. Apley
Assistant Examiner—Glenn E. Richman

[57] ABSTRACT

A system is shown to teach individuals the relationship between the visual size and the nutritional characteristics of portions of food by using either a life size image of, or the corporeal finger of the individual as a scale against life size images of different sized portions of different kinds of food, while showing the nutritional characteristics of such portions; and to adjust the relative sizes of portions of food to provide a nutritionally well-balanced meal.

43 Claims, 4 Drawing Sheets

FIG—1

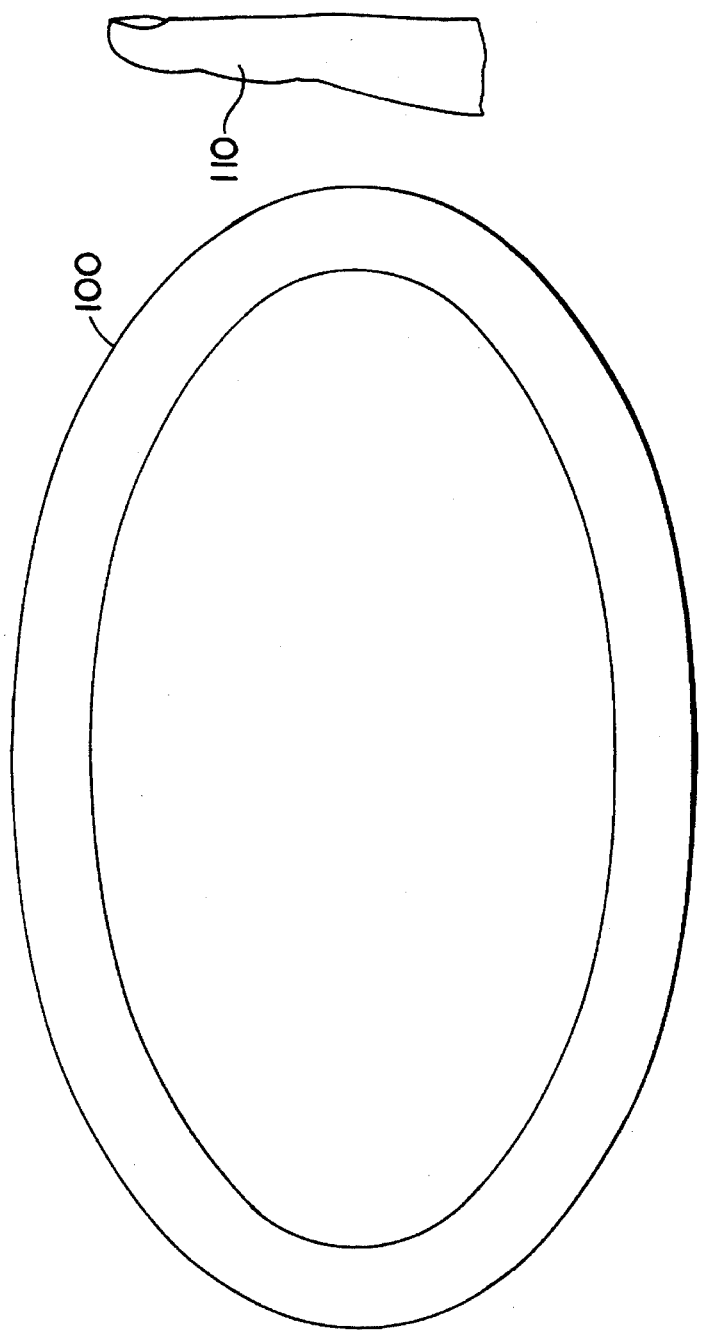
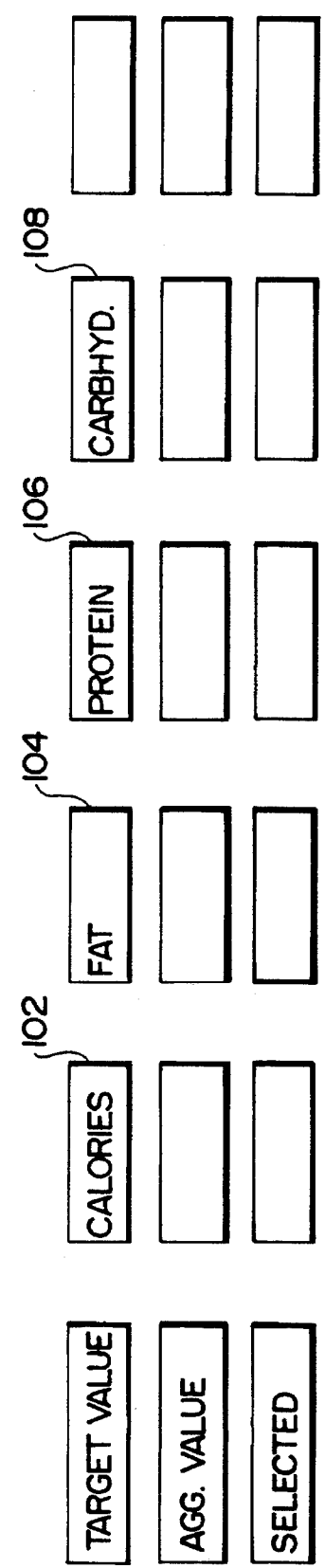
Fig - 3

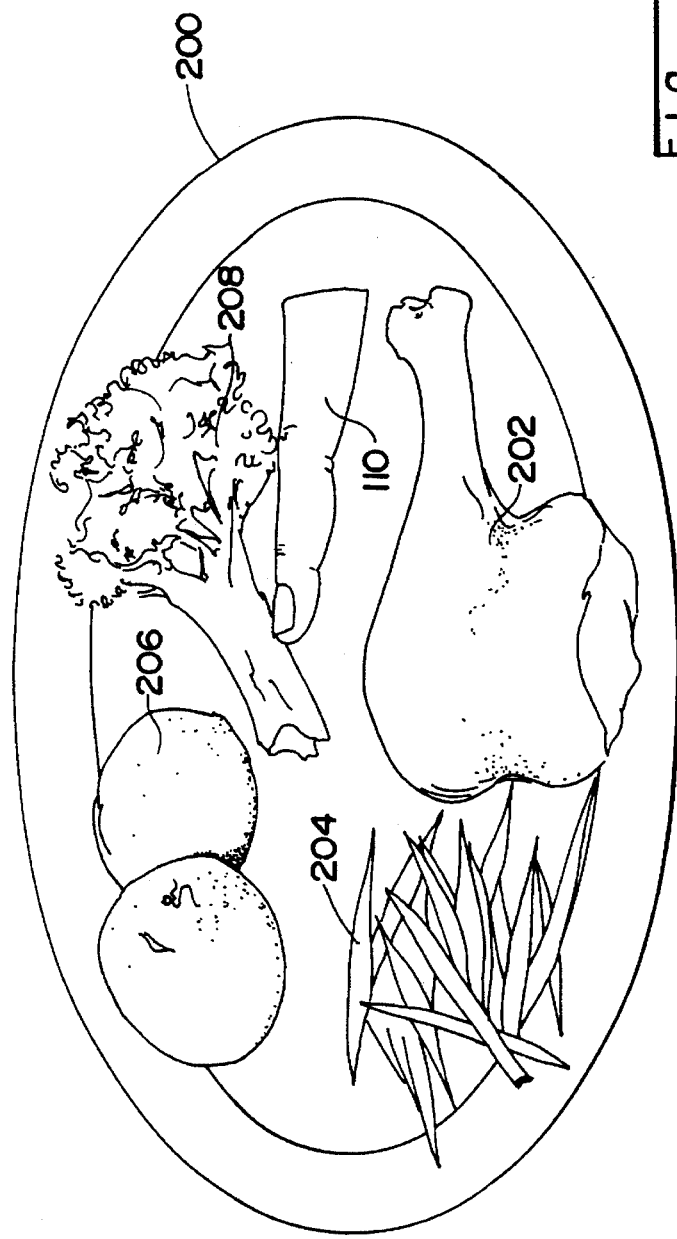

APPLICATION OF MULTI-MEDIA TECHNOLOGY TO NUTRITION EDUCATION AND DIET PLANNING

The disclosure of this patent document, including the drawing, contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND OF THE INVENTION

1. Field of the Invention

This invention relates to a method and apparatus for teaching individuals to estimate the size and attributes of objects; e.g., portions of food.

2. Description of the Related Art

Heart disease, stroke and diabetes are the three leading disease-specific causes of death in the US. Efforts to prevent these diseases or keep them in check have focused on diet, with or without exercise regimens, education and behavior modification programs.

Especially in the case of diabetes, prevention strategies center on diet. Obesity appears to aggravate the development of diabetes; and weight loss appears to reduce the risk of developing diabetes. In one study of obese individuals, after six years of follow-up, more than 50% of the subjects developed and an additional 30% showed impaired glucose tolerance. It has been known for more than 40 years that glucose tolerance can return to normal upon a reduction in body weight. Several recent studies demonstrate significant beneficial effects on carbohydrate and lipid metabolism without the necessity of obtaining ideal body weight. There would be an enormous positive effect if there were even moderate compliance with recommendations for a healthy diet.

The failure of the usual diet strategies is well known. A new technique for verifying actual food intake, the double water method has established the unreliability of self-reporting of food intake, especially by the obese. The doubly labeled water method measures integral $CO_2$ production from the difference in elimination rates of deuterium and 18Oxygen from labeled body water. Validations against near continuous respiratory gas exchange have demonstrated that the method has a 2 to 8 percent precision depending on the isotope dose and the length of the elimination period. [Schoeller DA. Measurement of energy expenditure in free-living humans using doubly labeled water. J Nutr 1988;118:1278–89.] The doubly labeled water method is non-invasive and nonrestrictive, but very expensive. It identifies misreporting but it does not indicate the possible causes for the errors.

Two recent studies indicate the standard recommended procedure for learning to conform to a diet regimen. Analyzing the reasons for the failure of self reporting suggests the need for better methods and or better tools.

Long term studies were performed by Lichtman et al. with free-living subjects at the Beltsville Human Nutrition Research Center over the past 14 years. [Lichtman et al. Discrepancy between self-reported and actual caloric intake and exercise in obese subjects. N Engl J Med 1992;327:1893–8.] Although there had been a suspicion of systematic under-reporting of food intake, most of the published data records were small, which may account for the fact that they created little discussion. In 1990 a large study of 266 free living volunteers, with no health problems, on a weight maintenance diet was conducted. [Metz et al. What are people really eating? The relationship between energy intake derived from estimated records and intake determined to maintain body weight. Am J Clin Nutr 1991;54:291–5.]

The subjects were given an initial one hour period of instruction in measuring and estimating techniques. The subjects were instructed by registered dieticians in groups of ten or less. The diet questionnaire was explained, there was demonstration and practice in the use of measuring scales, spoons and cups. Instruction was given on estimating portion size without measuring devices for meals eaten away from home. The participants took the measuring devices home, and were expected to measure their food portions at home. The dieticians scrutinized the diet records in the presence of the subjects on a daily basis, weekends excepted, to resolve any questions as to quantity, incomplete records, or vague descriptions. The subjects recorded their food and drink intake daily for at least seven days. They were admonished not to change their habitual life styles, particularly their physical activity. All meals were provided, including snacks, and milk and sweetener for coffee or tea. It is to be noted that weekday breakfast and dinner was consumed at the center, and lunch was consumed at work, so that the weighing and measuring tools which were taken home were, presumably used only for weekend meals at home. The mean difference between recorded and determined intake was an under-reporting of approximately 18% with no significant difference for sex, age or weight of the subjects. [Metz et al]

These data agree with the recent study from the UK by Livingstone et al. in which one week dietary records of trained subjects were found to underestimate the energy expenditure by more than 20% in 18 subjects and as much as 50% in three subjects.

Despite the difference in the background of the Beltsville population versus the UK population the proportion of subjects underestimating their energy intake was 81% in Beltsville versus 84% in the UK study. Two different methods were used to estimate energy requirements, the measured intake for long term weight maintenance used in Beltsville versus the measurement of energy expenditure measured by the doubly labeled water method used in the UK study.

The study reported by Livingstone et al. reflects extreme care in the training of 31 subjects representing a wide range of ages occupations and socioeconomic status in Northern Ireland. [Livingstone et al. Accuracy of weighed dietary records in studies of diet and health. BMJ 1990;300:708–12.] For seven days each subject recorded the weight of items of food and fluid consumed and of leftovers. They were given scales, logbooks and written instructions including examples of completed forms. The day before the recording started each subject was given a detailed explanation and shown the cumulative weighing technique and then repeated the procedure in the presence of the investigator to insure that he or she was competent in the technique. The subject's progress in weighing foods was monitored and the records checked for completeness and accuracy. Subjects were instructed to record brand names of foods and to provide a complete description of the method of preparation, cooking, and recipes for composite dishes. These records were used to adjust for losses during cooking.

For foods and fluids eaten away from home, a description of the food, place of purchase, and the price were requested. When possible the corresponding portions of food were bought and weighed. But if this was not feasible, then estimated weights based on the average portion eaten by the subject was used. The researchers concluded that the observed discrepancies arose largely from inaccurate estimates of habitual energy intake due to conscious or subconscious changes in normal dietary patterns or under-reporting or both. The results closely replicated the previous year's measurements. Two different investigators were used in the two studies which strongly suggests that the bias is not due to the observer but is inherent in the method and the impact of the test on the subject. "Bias may be greater than is generally appreciated, consequently the seven day weighed record may lose accuracy in an attempt to increase precision." [Livingstone et al.]

Interviews were conducted with the subjects after the study in which they all emphasized that the weighing protocol had interfered with their normal eating behavior, and they had difficulty in maintaining motivation particularly in the middle of the measurement period. Having to weigh snacks was named as the most onerous and irritating aspect of the procedure, and subjects admitted having omitted or simplified some measurements.

The report notes that over half of the people invited to participate in the study declined to do so and that it was most difficult to recruit those subjects who had previously been found to have low energy intakes. The present study was therefore probably weighted in favor of more highly motivated and compliant subjects. And thus the bias is unlikely to be an overestimate of either the frequency or the degree of error that would exist in more representative study populations.

Livingstone et al. is characterized by rigorously trained investigators who maintained a high level of contact with subjects who had received more that the usual level of training. The Beltsville study indicates almost as much training and supervision. The subjects were all deemed capable of accurate weighing, measuring and recording. Both groups were considered highly motivated. Furthermore, it is unlikely that over eighty per cent of the subjects would consciously and consistently underreport food intake by around twenty per cent. Both studies make clear that even under carefully controlled circumstances the weighing, measuring, recording protocol is too complex and too intrusive.

In considering why dietary self reporting is so problematic it is perhaps useful to consider what skills are actually represented in asking subjects to keep a diary. One skill is the ability to accurately weigh and measure food. A second skill is recording these measurements. A third skill is the ability to judge the comparative size of objects. A fourth skill is to make the association between the visualization of the food in a measured container to the free form volume of food on a plate.

The Lichtman and Livingstone studies show that subjects who were taught weighing and measuring skills and how to enter the results in a log were judged by nutrition professionals to be adequately proficient in these skills, underestimated their food intake substantially. Since the subjects were judged to be highly motivated, the intrusiveness of the recording method is one likely source of the errors.

A few studies made the attempt to measure the ability of the subjects to estimate the size of objects. In a study of subjects with anorexia nervosa, it is reported that Yellowlees set up a videotape of five high energy foods and four neutral objects of similar size. [Yellowlees et al. Abnormal perception of food size in anorexia nervosa. BMJ 1988;296:1689–90.] The videotapes were made so that the portion of food or the object was initially shown as an image on the screen at one half of its actual size and increased steadily over a minute's duration to twice its actual size. The value of the magnification appeared in the lower right hand corner of the screen but was covered by a tab during the experiment. The images of food were alternated with the neutral objects. A dummy television screen was placed to the right of the real TV screen and a corresponding real object was placed in the middle of the dummy screen. Using a remote control, the subject was able to stop the videotape when the image was estimated to be the same size as the real object in the adjacent dummy screen. When the subject was satisfied with the result, the experimenter lifted the tab and recorded the value of the magnification. In a second experiment the object was removed after ten seconds, and the subject was required to choose the videotape image from what was remembered of the real object. In the third experiment the object was shown without reference to the videotape, and the subject was asked to indicate its width by drawing a straight line on a blank sheet of paper. Whether or not the object remained in view was not stated in the report. In the Yellowlees study no difference was found between the group with anorexia and the control group in their ability to measure the size of neutral objects. Both groups did, however, noticeably exaggerate the size of foods. The subjects with anorexia perceived food as 12% larger than the control subjects did in each experiment. This significant difference highlights the psychological component to food size estimation.

In the Lichtman study it is reported that the subjects were given some version of the Yellowlees test to determine the ability of the subjects and ten of the controls to accurately estimate portion size. The subjects were asked to estimate the overall size (the linear dimensions, and the volume and weight of various standard foods.) As in the Yellowlees study, the results were expressed as a percentage of the actual weight or volume. The scores for both groups were practically perfect. The percentage of actual portion size identified by the subjects was 98±17 and for the controls was 96±11. In contrast, these same subjects under-reported their actual food intake by an average 47±16%; while the controls under-reported their energy intake by 19±38%. This suggests that it is not the inability to judge size, per se, that causes the inaccuracy of estimation of dietary intake.

Another study which suggests that it is not the inability to judge size, per se, which causes the under-reporting is reported by Lansky et al. [Lansky et al. Estimates of food quantity calories: errors in self-report among obese patients. Am J Clin Nutr and 1982;35:727–32.] In this study an attempt was made to directly test the assumption that size cues are affected by the size of the plate on which the food portions are presented. Five foods on large plates, and five foods on small plates were presented, all of the same size portion. Except for one food, cottage cheese, there was no significant difference between the estimates made for large and small plates. For cottage cheese, the subjects estimated that the small plate had fewer calories in its portion than the large plate. These subjects received no special training. They were asked to estimate the quantity of ten foods by weight or fluid ounces and then to estimate calories using a chart. These obese, dieting subjects underestimated quantity by 63.9 per cent and calories by 53.4 per cent [Lansky et al].

One of the implicit assumptions in the weighing, measuring and reporting protocol is that the individual will be able to make the association between the size of the food portion in the measuring utensil and the food encountered in a natural situation. The above analysis indicates that this failure of association may actually be the most significant contributor to the reporting error margins.

There is a known method used in teaching nutrition which addresses this issue. Realistic scale models of food portions as they appear on a plate are made out of composite materials. They are very expensive to make and a different object must be made for each different portion size for each food. The cost and unwieldy nature of this method keeps it from widespread use and testing. It is not a method designed for home use and storage problems would make it very intrusive.

The scale model method at least addresses the issue of the relationship of a food portion to a realistic visually perceived size. Other systems presuppose an intermediate step of numerical calculation by the individual. The most common source of nutrition information is printed on the labels of processed food which provides, inter alia, calories, fat, protein and carbohydrate content for each food portion in grams or milligrams, and the U.S. Recommended Daily Allowance of common nutrients for each food portion expressed in percentages. The size of the portion, however, is determined by the manufacturer without regard to any consistency from product to product. Frequently it is impractical to calculate a single portion without emptying the entire contents of the package.

A system for reducing the amount of numerical calculation is the "Exchange Lists For Meal Planning" promulgated by the American Diabetes Association, Inc. and The American Dietetic Association. This system utilizes six groupings of food: starch/bread, vegetables, milk, meat and substitutes, fruit, and fat. Within each group different sizes of portions of respective different kinds of food will provide the same number of calories. For example, in the starch group ½ cup of pasta and 1 slice of bread (each being one starch exchange unit,) will each provide 80 calories; and in the meat group 1 ounce of cooked poultry, fish or meat and ¼ cup of cottage cheese (each being one meat exchange unit,) will each provide 75 calories. A healthy daily diet of 1200 calories per day, can consist of 4 starch units, 5 meat units, 2 vegetable units, 2 fruit units, 2 skim milk units, and not more than 3 fat units per day. The distribution (and quantity) of the calories and groups over the several meals of the day is left to a dietician to prescribe (e.g., 25%, 35% and 45%,) for the specific needs of the specific patient. Serving sizes are taught by weighing or measuring out the food, e.g., ounces, grams, cups, and teaspoons.

Weighing and measuring is at the heart of all known systems for calculating the size of a food portion. The calculation is then associated with a visualization of the size of the portion either associated with the means of measuring or, as an additional step, as it would appear in a real life setting. The goal for the individual using the system is to recognize the total correct portion sizes for a customized best diet for that individual.

This invention offers a direct method for learning portion sizes appropriate to each individual, a non-intrusive method of remembering and checking the correct size of a portion, and a sense of the relative portion sizes appropriate to the individual's total diet.

SUMMARY OF THE INVENTION

The nature and substance of the invention includes a method and apparatus for displaying information relating to a characteristic of an object, comprising:

providing a storage means containing data for displaying images of different kinds of objects and for each kind of object relating to different sizes of each of said kind of objects;

providing a database containing data relating to different kinds of characteristics in appropriate units of measurement of each of said kinds of objects and for each kind of characteristic relating to said different sizes of each of said kind of objects;

selecting a particular kind of object;

selecting a particular kind of characteristic and appropriate units of measurement;

displaying an image of said selected kind of object in a selected size of such image; and displaying that datum which relates to the selected characteristic of the selected size of the selected kind of object.

It is therefore an object of the present invention, with respect to objects which are portions of food, to provide the user with realistic simulations of food portion sizes as they are encountered in daily experience, linked to self selected data in sufficient quantities that a pattern is discernible as to the portion sizes the individual should be eating.

It is another object of this invention to provide the user with a non-intrusive memory enhancer and reality check for congruence of the actual portion size with the user's visualized portion size.

It is yet another object of this invention provide an interactive information handling system which teaches the user to estimate the size of portions of food in preparation or prepared or eaten as is.

Still another object of the present invention is to provide a system which teaches the user to estimate the balance of the protein-carbohydrate-fat content for a given calorie meal.

A feature of this invention is the use of a life-size image of the user's own finger as a scale against which life-size images of portions of food are sequentially displayed with a selected unit of measurement respectively displayed for each food portion, to develop skill in estimating the quantity of such measurement units in various food portions.

Another feature is the use of life-size images of prepared foods on a platter, different foods being substituted for others, but each image displaying a well-balanced combination of foods in size and kind for a given calorie meal, to develop a sense of familiarity and "rightness" about the look of a well-balanced meal.

Another feature of this invention is to allow access to nutrition information, in the numerical units with which the individual is most comfortable, by pointing to the size of a life sized realistic illustration of the food portion.

BRIEF DESCRIPTION OF THE DRAWING

These and other features and advantages of the invention will be apparent from the following description of the invention taken in conjunction with the accompanying drawing in which:

FIG. 3 is a display of the monitor screen at the start of the use of the "well-balanced platter" feature; and FIG. 4 is a display of the monitor screen showing the customized choices of a user approaching the achievement of a "well-balanced platter".

DESCRIPTION OF THE PREFERRED EMBODIMENT

Figure 1:
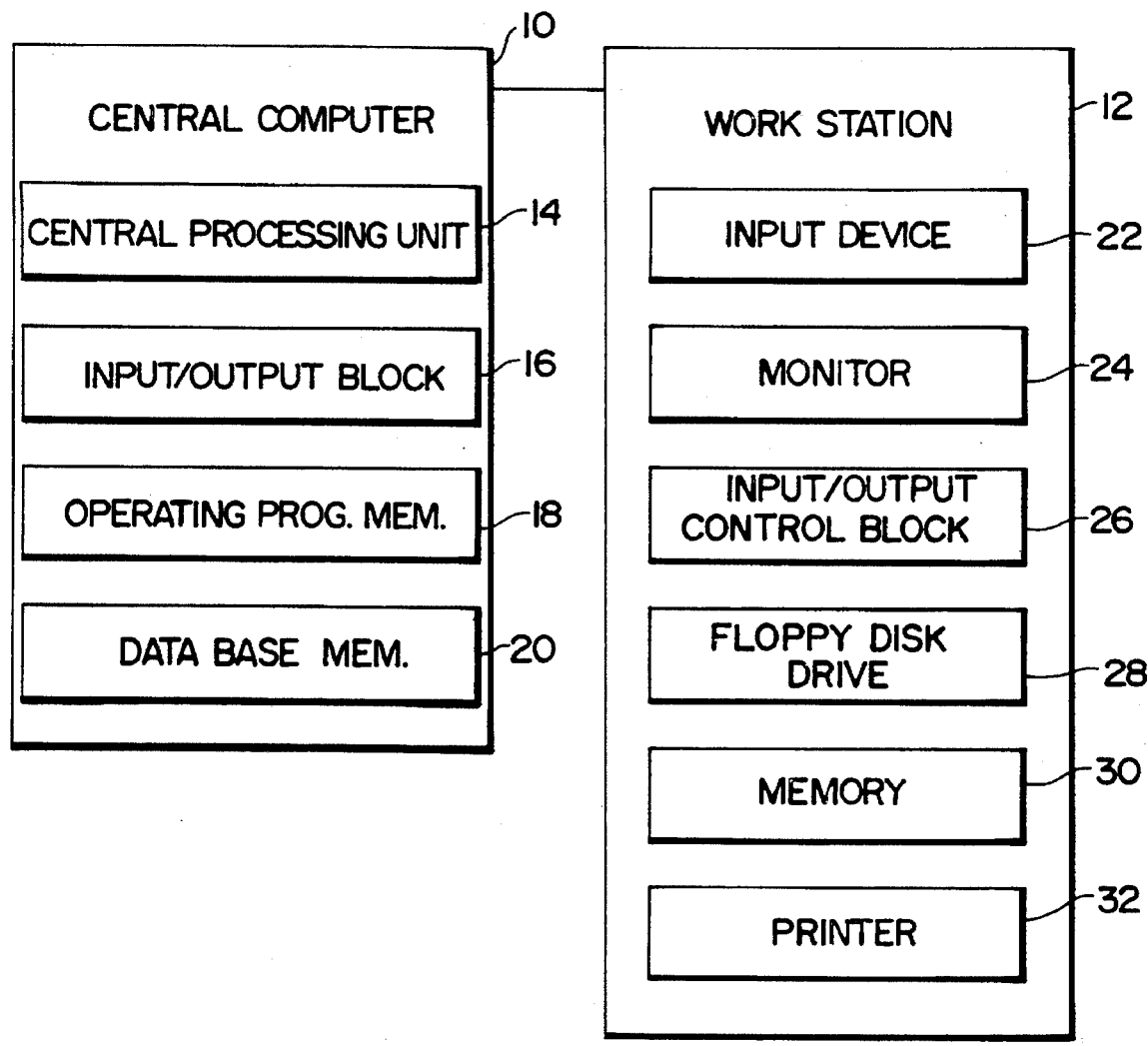
FIG. 1 is a block diagram of an interactive data handling system having a remote memory store which may be employed in the practice of this invention.

FIG. 1 shows a preferred embodiment of this invention having a central computer 10 and one or more work stations 12 which may be remote from, but coupled to, the central computer. The central computer has a central processing unit 14, an input/output control block 16, an operating program memory 18, and a database memory 20. Each work station has an input device 22, (which may be a keyboard, a mouse, a game controller, a voice recognition device, or a touch screen function of the monitor,) a monitor 24, and an input/output control block 26. The database memory 20 is used to store data relating to images of different kinds of objects, herein described as foods, in respective base sizes, and algorithms used to manipulate the base sizes into all desired sizes to be displayed, and the data relating to, and to be displayed in conjunction with each desired size. The database memory 20 is also used to store data relating to images of index fingers in respective base sizes, and algorithms used to manipulate the base sizes into any desired size and color to provide a life-size and life-like color image of the user's own finger. An index finger is preferably utilized for dexterity convenience but any finger may be utilized. The control block 26 permits the work station to be coupled to the central computer by any suitable means, such as a network, optical, or wired or wireless communication lines.

Additionally, but not necessarily, the work station of FIG. 1 may also include a floppy disk drive 28 to input portable files of data relating to the dietary restrictions of the individual user and to be used in conjunction with the computer database; a memory 30; and a printer 32.

Figure 2:
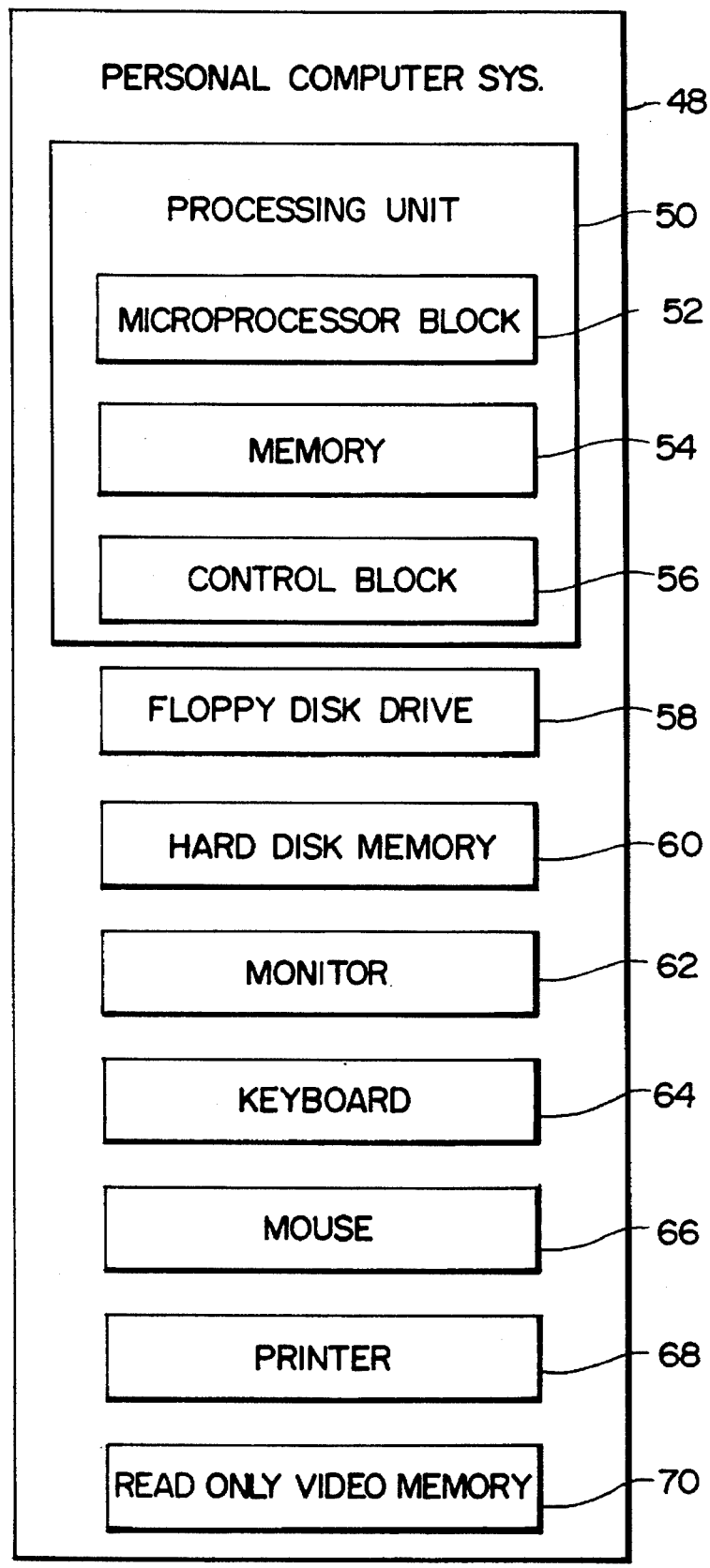
FIG. 2 is a block diagram of a self-contained interactive data handling system which may be employed in the practice of this invention.

Alternatively, FIG. 2 shows the functional components of a conventional personal computer system 48 which may employed in the practice of this invention. It has a processing unit 50 which includes a microprocessor block 52, memory 54, and a control block 56 which functions to control input-output function and the interactions between a floppy disk drive 58, the microprocessor block 52, the memory 54, and a hard-disk memory 60. The system also has a monitor 62, a keyboard 64, a mouse 66, a printer 68, and a read-only video memory 70. The video memory may be a videodisc player capable of playing one or more videodiscs, each of which can store up to 56,000 individual images, each randomly accessible, or a CD-ROM, or a digital data memory, or similar image storage system. The system also includes appropriate software, such as a system operating program, e.g., DOS and drivers for the video memory and other peripherals, and application programs which can generate, scale, move and rotate images and other programs which can manipulate databases.

In the preferred utilization of the system of FIG. 1, images of all foods are stored as data in a digital database. The images of portions of the same kind of food, which within a predetermined range or group of sizes, show the same visual structure but in different sizes, are generated from the same base data.

The images of the same food in the next predetermined range but having a different visual structure are made by recalculating from second base image data. Data may be stored for as many base images as is required to represent a realistic sizing of the food portion. Examples of different visual structures needed to show variation in portion size are: an image of a chicken leg can only be made so large before it looks like a turkey leg, therefore, to make it larger than a realistic size, a portion of thigh is added; an uncooked apple must show missing segments to make it realistically appear smaller. On the other hand, another base image would not be required to show a portion of applesauce which can be scaled larger and smaller and still appear realistic. Among the attributes of the image to be displayed which the algorithms calculate are: the size of the image, the compression ratio of the file, the location of the image on the screen, the horizontal and vertical orientation of the image, any overlapping with other images of other displayed objects, the color of each pixel of the image, and the degree of transparency of the color of each pixel of the image.

The different foods may be selected by the user for display by any one of several different modes of operation, or a combination thereof. The name of the food may be typed on the keyboard. Alternatively, the Food Pyramid may initially be displayed. The user, using the mouse, or the touch-screen function, selects a food type. Icons or small pictures of different foods of the selected type are then displayed. The user, using the mouse, or the touch-screen function, selects a particular food. Yet alternatively, the user may browse seriatim through a store of pictures and select those of interest. The images of food (and their related characteristics,) may be stored and displayed as unprepared, or prepared according to different recipes, e.g., raw chicken, roast chicken, chicken in red wine sauce, etc. The data relating to the characteristics in appropriate units of measurement (e.g., calories, joules, grams, ounces, % of RDA, exchange units,) of each of the particular foods are stored and accessed as a function of the size of the displayed image of each such food.

Images of fingers are stored as data from which can be calculated a plurality of visual images of fingers of different proportions and skin color. The user can select a particular finger of a particular hand, proportion and color, and can scale the finger, as required, so that the image of the finger on the monitor is identical in dimensions to the user's own selected finger. This can be done by contact with the screen of a touch screen monitor, by moving and clicking the mouse, or by striking the arrow keys on the keyboard. Thus the user creates on the monitor a scale, i.e., the finger, which is identical to a scale which the user carries always and to all places, including the kitchen and the restaurant. The image of the finger can be moved in location and in orientation on the screen so that it can serve as a scale or as a cursor (pointer) or both. Similarly, the user can change the size of a displayed image of a portion of food by moving the cursor by touching the touch screen, using the mouse, using the arrow keys, or using the image of the finger (as the cursor.) If the user's corporeal finger is part of the system, as with a touch screen, then the image of the finger on the screen may be omitted and the characteristics of the corporeal finger used instead.

In a further utilization of the system of FIG. 1, other images which are linked visually to a food image, e.g., pasta with sauce, may be calculated from a different base image from the food shown singly, or the linked images can be calculated from separate base images though appearing on the screen together, e.g. a skinless chicken portion overlaid with a separate image of skin appears to the viewer as a piece of chicken with skin.

In the utilization of the system of FIG. 2, data for each image in each size is stored separately as fixed data, e.g., a large plurality of visual images are stored on one or more videodiscs each individually and randomly addressable. Variations, e.g., food with or without sauce and for each size, require a separate stored image for each variation.

In all cases, the size of the displayed food image is linked to databases in the main memory store of the system. For each calculated food image size or for each address on the videodisc, i.e., for each kind of food and size of portion, there is stored the respective nutrient content measurement in different categories of units, e.g., milligrams of vitamins, milligrams of minerals, calories, grams of protein, grams of carbohydrate, grams of saturated fat, grams of unsaturated fat, grams of cholesterol, percentage of Recommended Daily Allowance of any of the foregoing, food exchange units, and ounces or grams of weight, or fluid ounces, tablespoons and other measurements of volume. The user can select the category or categories of units of measurement that are to be displayed on the monitor. Thus the user may display concurrently on the screen: an image of any kind of food, cooked or uncooked, and any size of portion; any one or more categories of nutrient content of the food portion expressed in units of any system of measurement; and the immutable, constant-size finger of the user. The image of the food portion will be displayed with the immutable finger and whatever category or categories of nutrient content and units of measurement the user has also selected. For example, the user can select a food and, as the selected size of the displayed image varies, see a corresponding readout in calories or exchange units. The user can call up a food portion in calories, and have the related ounces or food exchange units displayed. Thereby the user learns the characteristics of food in the nutritional units with which the user is most comfortable in sizes related to the ever present user's own finger. It is not necessary to remember the numbers of the units but only the visualization of the desired size compared to the user's finger. The user may select as many individual items of food, with accompanying individual readouts, as will fit on the screen.

Instructional games can be included in the program to test the user's ability to judge sizes of food portions. The game can present any, or a series of images of food portions, and allow the user to input an estimate in the unit of measurement the user has practiced, such as their respective weights or calorie content or food exchange values, or protein, carbohydrate, fat content, and have a visual reward displayed if the answer is correct, or the correct answer if the answer is not correct. The visual reward may be in the form of an entertaining, short duration, animated sequence of images which may be unrelated to food and nutrition, and provide a respite from the instruction. An answer may be considered correct if it is similar to the stored value. Similarity may be defined in accordance with the accuracy required by the course of instruction; e.g., plus or minus five percent.

Nutrition education also requires understanding of how an individual portion must be adjusted to account for other foods eaten in that meal and in the total daily diet. The same or similarly stored images described above may be presented on the screen in a coupled manner so that the size of one portion affects the size and readouts of the other selected food images. The user may select as many coupled items of food, with accompanying individual readouts, as will fit on the screen. A purpose is to develop a visual sense of how altering one food portion should trigger a change in other food selections.

Meal planning can be taught using the concept of a well-balanced platter. A well-balanced platter is an assembly of food images displayed on a plate as a particular meal which represents an appropriate percentage of the minimum daily requirements for food nutrients, distributed as to food groups and protein, fat and carbohydrate balance, as exemplified by the ADA Food Exchange lists, and totalling a given number of calories for the particular meal or snack.

The user, in answer to program prompts, enters the unit or units in which the user wishes the characteristics of selected foods to be displayed—such as US Dept. of Agriculture Minimum Daily Requirements, or American Dietetic Association Food Exchange Units, and the values of these characteristics are displayed in these units on the screen.

In response to program prompts, the user enters the user's own pertinent characteristics and the program will display or compute and display the target values for one or more characteristics for that platter expressed in the selected units. FIG. 3 shows an empty platter 100 with a series of target values in the selected units of the selected characteristics (calories 102, grams of fat 104, grams of protein 106 and grams of carbohydrates 108,) and a life-size image of the user's own index finger 110.

The user selects food items for a well-balanced platter from a menu of stored food images. Each food image is stored in a respective size of a conventional single portion with respective nutritional data linked thereto. A food image may have linked thereto other food images which are dependent on the size of the displayed food image, e.g., leg and leg plus thigh. A food image may have linked thereto other images which are optional, e.g., sauces, or skin.

When the user selects a first food item for the platter, there is a readout or readouts in the selected units of the selected characteristics of the size of food item as its image is stored, i.e., a conventional single portion. The user can select to be displayed on the screen any combination of individual and aggregate values for the food portions displayed on the plate. Changing the size of any food image changes the respective readouts. Second and subsequent food items chosen for display are coupled to the first item so that a change in the size of one affects the size of the others if it is necessary so as not to exceed the target aggregate values. For example, if the target is six grams of fat, selection of a next food item will proportionally reduce the size of prior selected food items if necessary to maintain a food platter whose aggregate grams of fat does not exceed six grams.

When the user selects a next food item, the user may elect to override the automatic coupling and manually adjust the relative sizes by using an aggregate readout in the selected units of the selected characteristics for the platter. The user may change the size of the images, to less or more than a conventional portion and thereby change the value of the aggregate readouts. The user may select a reasonable number of food choices and respective image sizes. The user's finger is also shown. Using the mouse, the user can move and orient the image of the finger as a cursor adjacent to any of the food portions, and then use the image of the finger as a scale and as a means to change the size of the image of the portion. FIG. 4 shows an override mode of operation with a platter 200 having four items of food thereon, i.e., chicken 202, green beans 204, potatoes 206, and broccoli 208, and the life-size image of the user's finger 110 serving as a cursor to point to a selected item, i.e., broccoli. Also shown are the target values in calories: 600 210, grams of fat: 10 212, grams of protein: 50 214, and grams of carbohydrates: 75 216; the aggregate values of the food items on the platter in calories: 556 218, grams of fat: 9.1 220, grams of protein: 54.9 222, and grams of carbohydrates: 67.3 224; and the values of the selected food item (broccoli) in calories: 26

226, grams of fat: 0.3 228, grams of protein: 3.1 grams of carbohydrates 4.5 232, and ounces of gross weight 3.5 234. Readouts for saturated fat, unsaturated fat, cholesterol, etc., can also be shown. The user can fine-tune the size of the broccoli so that the aggregate values most closely meet the target values. In this example, the user is on a normal calorie diet, but with a restriction on fat. The user can double or even triple the volume of broccoli without exceeding the target values within allowable tolerances. While only a single platter is shown here, obviously additional plates can be shown with side dishes or desserts. Further, while the readouts have been selected by the user to show grams, other units of measurement, such as RDAs, can be selected.

If and when the user makes an error in which the size (or some other chosen parameter,) of the next selected food item causes the aggregate total to unreasonably exceed the target value limitation for the user's diet, the immediately prior configuration will be restored, a warning signal presented, and hints for better food item selection will be offered.

The user can also start with well planned menus of various kinds provided by the program in categories, such as: ethnic, low cost, or a particular holiday. The purpose of all balanced platter exercises is to develop in the user a sense of familiarity and "rightness" about the look of a well-balanced meal. The sense of familiarity is enhanced by the invariable presence of the user's own finger or the life-size image of the user's own finger in proximity to life-size images of the plate displaying the aggregate of the food portions.

A well-balanced platter game may be played by the members of a family. A "family" is a group of people who habitually eat together, and at least one of whose members is the maker of the meal for the family. The principal purpose of the game is to aid the meal maker in adapting a menu to the particular needs of the individual members. Another purpose is to make each member aware of the adjustments needed by each of the other members, and, therefore, more supportive of the other members in their efforts to adhere to their respective individualized diet regimen. A third major purpose is to give each member a sense of "rightness" or "correctness" when encountering a nutritionally well-balanced meal.

A well-balanced platter as used in the game is a particular meal consisting of different food items from the different food groups representing a percentage of the minimum daily requirements for food nutrients, balanced for protein, fat and carbohydrates, with an aggregate calorie count for an "average" person. Images of pre-planned platters may be grouped into categories such as breakfast, midday meal, and evening meal; and holiday meals, ethnic meals, and quickly prepared meals. These images may be displayed and the family selects a particular platter.

In response to program prompts, each family member enters into the system her pertinent characteristics which are her game goals, e.g., total calories, recommended protein, fat and carbohydrate units, diet restrictions or supplements. Total daily requirements may be appropriately apportioned by the particular meal, e.g., breakfast at 25%, midday meal at 35%, and evening meal at 40%. The system may allow minor adjustments and substitutions to be made to the choice of food items presented on the plate.

The game point scheme is displayed and explains how the difficulty of the changes needed to individualize the starting parameters are weighted. There are visual rewards to be displayed for correct answers and diagnostics for errors. Each player family member will be scored on the number of errors made to reach a correct answer. A response will be counted as correct if it is similar to the system stored answer. Similarity may be defined in accordance with the accuracy required by the needs of the family members. If a member is at risk for a life threatening medical condition, the allowed deviance for an aggregate selected unit count may be much smaller than if no members of the family have special needs. Images of pre-planned platters may be grouped into categories such as breakfast, midday meal, and evening meal; and holiday meals, ethnic meals, and quickly prepared meals. These images may be displayed and the family selects a particular platter.

The game is optimally played with all of the family members participating. After the particular well-balanced platter has been selected, each player in turn may change the size of each and any food image on the plate. The size of each food image on the plate is linked to the respective sizes of the other food images to maintain constant the aggregate number of calories for the platter. However, a manual over-ride of the linkages is permitted to enable one food image to be changed without affecting the sizes of the other images. In such a case, all values, including aggregate calories, are displayed at their current, correct magnitudes. If any current magnitude is grossly out-of-bounds, a warning signal is displayed.

Some food items may have linked other food items which are optional, e.g., sauces, skin. The program may offer a limited number of substitutions for a given food item.

If an error is made in which the size or another chosen parameter unreasonably exceeds the limitations for the player's diet, then the former configuration will be restored on the display, or will alternate on the display with the erroneous configuration; a warning signal will be displayed, and hints will be offered. The object is to have each player end her turn with a correct configuration of a well-balanced platter. To that end, a player who is "stuck" will be provided with prompts, the correct responses to which will lead to a correct configuration.

Levels of difficulty may be added to the game by adding food preparation alternatives either verbally or as additional food images.

The game may be played by a single player and used to assess her food planning skills.

A print-output may be provided for the platters of each of the players. The aggregate of all the respective correct platters of all of the player family members may be displayed and printed as a game finale to instruct the meal making member of the family as to what volume of each food item should be prepared and served to the family to enable each member to meet her limitations for her diet.

While a particular embodiment of the present invention has been disclosed, it is to be understood that various different modifications are possible and are contemplated as being within the true spirit and scope of the claims. There is no intention, therefore, of limiting this invention to the exact abstract or disclosure presented herein. More particularly, it is contemplated that this invention can be used with any system of objects having different sizes and different information related to the kind of object and the size of the particular kind of object.

What is claimed is:

1. A method of displaying information related to a characteristic in appropriate units of measurement of an object, comprising the steps of:

providing a storage means containing data for displaying images of different kinds of objects and for each kind of object relating to different sizes of each of said kind of objects;

providing a database containing data relating to different kinds of characteristics in appropriate units of measurement of each of said kinds of objects and for each kind of characteristic relating to said different sizes of each of said kind of objects;

selecting a particular kind of object;

selecting a particular kind of characteristic and appropriate units of measurement;

displaying an image of said selected kind of object in a selected size of such image; and displaying that datum which relates to the selected characteristic of the selected size of the selected kind of object.

2. A method according to claim 1, wherein:

the size of such image is selected by the substeps of:
displaying an image of said selected kind of object; and
manipulating the size of the displayed image to obtain the selected size of the image.

3. A method according to claim 1, wherein:

the size of such image is selected by the substeps of:
selecting a datum which relates to the selected characteristic and the corresponding size of such image is automatically selected.

4. A method according to claim 2, further including the steps of:

manipulating the size of the displayed image to a different size of said selected kind of object; and displaying that data which relates to said selected characteristic, said selected kind of object, and said different size of the selected kind of object.

5. A method according to claim 1, further including the steps of:

selecting a different size of said selected kind of object;

displaying an image which relates to said selected kind of object in said selected different size; and displaying that data which relates to said selected characteristic and said selected object and said selected different size of the selected object.

6. A method according to claim 1, further including the steps of:

selecting a different kind of object in the same size and for the same characteristic as the previously selected kind of object, and displaying that data which relates to said selected different kind of object and said same size and said same characteristic.

7. A method according to claim 1, further including the steps of:

providing a storage means containing data for displaying an image of a particular portion of human anatomy, in different shapes and in different sizes;

selecting and displaying that shape and size image which most closely resembles said individual's own particular portion of anatomy; and utilizing the displayed image of said individual's own particular portion of anatomy as a visual scaling factor for the displayed images of the objects.

8. A method according to claim 7, wherein:

said particular portion of human anatomy is a finger.

9. A method according to claim 7, wherein:

each of said anatomy images which is to be displayed is individually stored as fixed data.

10. A method according to claim 7, wherein:

the data for an image of anatomy are individually stored as base data; and algorithms are utilized to perform calculations on the stored base data to generate the display of the anatomy image.

11. A method according to claim 10, further including the substeps of:

selecting the visual orientation of the image of anatomy as displayed.

12. A method according to claim 10, further including the substeps of:

selectively varying the orientation and location of the image of anatomy as displayed.

13. A method according to claim 10, further including the substeps of:

utilizing the image of anatomy as a life-size cursor;

certain of said anatomy images which are to be displayed are individually stored as base data; and others of said anatomy images which are to be displayed are generated by changing one or more dimensions of the respective base data whereby to change the respective dimensions of the respective other of said images.

14. A method according to claim 10, wherein: each of said anatomy images may be changed to a selected color.

15. A method according to claim 1, further including the steps of:

selecting a particular corporeal portion of the individual's anatomy and using it as a visual scaling factor for the displayed images of objects.

16. A method according to claim 15, wherein:

said particular portion of human anatomy is a finger.

17. A method according to claim 1, further including the step of:

the individual using the individual's own, corporeal, and visible finger as an aid to memory in associating the size of the displayed image of the object with the displayed data relating thereto.

18. A method according to claim 1, further including the step of:

the individual learning to associate the data relating to the specific characteristic relating to the selected size of the selected object with the displayed image of the selected size of the selected object.

19. A method according to claim 1, wherein:

said objects are portions of food.

20. A method according to claim 19, wherein the characteristic is the nutrient content in appropriate units of measurement taken from the group consisting of:

vitamins, minerals, calories, protein, carbohydrate, saturated fat, unsaturated fat, and cholesterol.

21. A method according to claim 19, wherein said objects are portions of food before preparation and serving.

22. A method according to claim 19, wherein said objects are portions of food after preparation and serving.

23. A method according to claim 1, wherein:

as the selected size of the selected object varies, the proportions and the shown structure of the related image of the object varies so that said image is lifelike on a one to one scale.

24. A method according to claim 23, wherein:

when the selected size of the selected object is within a first predetermined range, a first predetermined visual structure of the selected object is displayed in the image of the selected object;

when the selected size of the selected object is within a second predetermined range which is greater than said first predetermined range, a second predetermined visual structure containing more structure than said first predetermined visual structure of the selected object is displayed in the image of the selected object; and when the selected size of the selected object is within a third predetermined range which is smaller than said first predetermined structure, a third predetermined visual structure containing less structure than said first predetermined visual structure is displayed in the image of the selected object.

25. A method according to claim 1, further including the substeps of:
after the selection of a particular kind and size of the object and the display of the respective image; and
prior to the display of that data which relates to the selected characteristic of the selected size of the selected object;
requiring the individual to select for display the individual's own choice of that data which relates to the selected characteristic of the selected size of the selected object.

26. A method according to claim 25, further including the substeps of:
comparing the individual's choice of data with the data from the database which relates to the selected characteristic of the selected size of the selected object, and if the data are similar, then providing the individual with a reward and displaying the relevant data from the database.

27. A method according to claim 26, further including the substeps of:
after comparing the data, and if the data are not similar, then omitting the reward and displaying the relevant data from the database.

28. A method according to claim 1, further including the substeps of:
contemporaneously selecting a plurality of different kinds of objects, and respective sizes thereof;
concurrently displaying the respective images of the selected objects; and
displaying that data which relates to the aggregate of the selected characteristic of the selected sizes of the selected objects.

29. A method according to claim 28, wherein:
the objects are portions of food.

30. A method according to claim 1, wherein:
each of said object images which is to be displayed is individually stored as fixed data.

31. A method according to claim 1, wherein:
the data for an image of an object are individually stored as base data in a respective file; and
algorithms are utilized to perform calculations on the stored data to generate the display of the image.

32. A method according to claim 31, wherein:
the algorithms calculate one or more of certain attributes of the image to be displayed, which attributes consist of:
compression ratio of the file,
size of the image,
color of each pixel of the image,
degree of transparency of the color of each pixel of the image,
location of the image in the display,
horizontal and vertical orientation, and
the overlap with another image of a displayed another object.

33. A method according to claim 31, wherein:
the different images of a kind of object are sorted into groups, wherein each image in a particular group has the same visual structure.

34. A method according to claim 1, further including the substeps of:
contemporaneously selecting both
(i) a plurality of different kinds of objects and
(ii) the aggregate of a selected characteristic in appropriate units of measurement of said selected objects; and
concurrently displaying in combination respective images in respective sizes of the respective selected kinds of objects, wherein the aggregate of the selected characteristic is equal to the selected aggregate.

35. A method according to claim 34, wherein:
each of said objects is a portion of food.

36. A method according to claim 34, further including the substeps of:
sequentially displaying different combinations of said respective images, wherein for each of said combinations the displayed aggregate of the selected characteristic is equal to the selected aggregate.

37. A method according to claim 36, wherein:
each of said objects is a portion of food.

38. A method according to claim 1, wherein:
said image data is provided from a remote storage means; and
said characteristic data is provided from a remote database.

39. A method of teaching an individual to estimate the size of an object, comprising the steps of:
providing a storage means containing data for displaying images of different sizes of an object;
displaying an image of the object in a selected size;
providing a storage means containing data for displaying an image of a particular portion of human anatomy in different shapes and sizes;
selecting and displaying that shape and size image which most closely resembles said individual's own particular portion of anatomy; and
utilizing the displayed image of said individual's particular portion of anatomy as a visual scaling factor for the displayed images of the object.

40. Apparatus for practicing the method of claim 1, comprising:
storage means containing data for displaying images of different kinds of objects and for each kind of object relating to different sizes of each of said kind of objects;
database means containing data relating to different kinds of characteristics in appropriate units of measurement of each of said kinds of objects and for each kind of characteristic relating to said different sizes of each of said kind of objects; and
means, coupled to said storage means and said database means, for
selecting a particular kind of object,
selecting a particular kind of characteristic,
displaying an image of said selected kind of object in a selected size of such image, and
displaying that datum which relates to said selected characteristic in appropriate units of measurement of said selected size of said selected kind of object.

41. Apparatus according to claim 40 wherein:

said storage means data includes data relating to images of different kinds of foods in different sizes of portions; and said database means data includes characteristics relating to nutritional characteristics in appropriate units of measurement of each of the different portions of the foods.

42. Apparatus according to claim 40, further including:

additional storage means for containing data for displaying an image of a particular portion of human anatomy in different sizes and in different shapes; and said selecting means has a mode of operation wherein a user may select an anatomical image of a particular size and shape.

43. Apparatus according to claim 40, wherein:

said selecting means has a mode of operation wherein:

the selection of the kind of object, the selection of the size of the selected kind of object, and the selection of the particular kind of characteristic and the appropriate units of measurement provides a display of that datum which relates to the combination of said selected object, size, and characteristic, and the selection of the kind of object, the selection of the particular kind of characteristic, and the selection of the particular datum of the particular kind of characteristic, provides a display of that image in that size which relates to the combination of said selected object, size, characteristic, and datum.

* * * * *